United States Patent [19]

Hagiwara

[11] Patent Number: 5,753,250
[45] Date of Patent: May 19, 1998

[54] CRYSTALLINE ANTIMICROBIAL COMPOSITION

[75] Inventor: Zenji Hagiwara, Kusatsu, Japan

[73] Assignee: Hagiwara Research Corporation, Amagaski, Japan

[21] Appl. No.: 583,999

[22] Filed: Jan. 11, 1996

[30] Foreign Application Priority Data

Jan. 12, 1995 [JP] Japan ................... 7-018793

[51] Int. Cl.[6] ................... A01N 25/08; A01N 25/34; A61K 9/14

[52] U.S. Cl. ................... 424/405; 424/409; 424/414; 424/417; 424/421; 424/489; 424/618; 424/630; 424/641

[58] Field of Search ................... 424/405, 409, 424/414, 417, 421, 489, 618, 630, 641

[56] References Cited

U.S. PATENT DOCUMENTS

| | | | |
|---|---|---|---|
| 1,920,492 | 8/1933 | Zellman | 424/618 |
| 3,159,536 | 12/1964 | Marotta | 424/421 |
| 4,906,466 | 3/1990 | Edwards et al. | 424/78 |
| 4,911,898 | 3/1990 | Hagiwara et al. | 423/118 |
| 4,911,899 | 3/1990 | Hagiwara et al. | 423/118 |
| 4,929,431 | 5/1990 | Hagiwara et al. | 423/328 |
| 4,959,268 | 9/1990 | Hagiwara et al. | 423/403 |
| 5,244,667 | 9/1993 | Hagiwara et al. | 424/409 |

FOREIGN PATENT DOCUMENTS

| | | |
|---|---|---|
| 0251783 | 1/1988 | European Pat. Off. . |
| 0116865 | 8/1994 | European Pat. Off. . |

OTHER PUBLICATIONS

European Search Report for EP91–30–1660.

*Primary Examiner*—Thurman K. Page
*Assistant Examiner*—Kathryne E. Shelborne

[57] ABSTRACT

The present invention relates to a novel crystalline antimicrobial composition comprising silicon dioxide as a major component. More particularly, the present invention is concerned to said crystalline antimicrobial composition wherein said crystalline silicon dioxide contains silver ions and one or two optional metal ions selected from the group consisting of zinc and copper. Furthermore, the present invention relates to an antimicrobial ceramic composition comprising said antimicrobial composition.

17 Claims, 1 Drawing Sheet

# CRYSTALLINE ANTIMICROBIAL COMPOSITION

BACKGROUND OF THE INVENTION

The present invention relates to a novel crystalline antimicrobial composition comprising silicon dioxide as a major component. More particularly, the present invention is concerned to a crystalline antimicrobial composition comprising a silicon dioxide type crystalline structure as a predominant component and having an excellent heat resistance and weatherability. Furthermore, the present invention relates to an antimicrobial ceramic composition comprising said antimicrobial composition.

An antimicrobial composition having an antimicrobial aluminosilicate provided coating on the surface of silica gel, wherein said aluminosilicate containing metal ions possessing a microbicidal activities selected from the group consisting of silver, zinc, copper, mercury, tin, lead, bismuth, cadmium, and chromium is well known. Since said antimicrobial composition is effective against common fungi and also exhibits excellent biocidal activity against mildew, research and development leading to new applications have been carried out, extensively.

It is known however, that an undesirable discoloration or coloration in addition to a change in the properties of the molded article occur when a polymer containing the silica gel based amorphous antimicrobial composition described above is molded at an elevated temperature. The properties of the molded article vary as a function of time. These problems have remained unresolved.

The object of the present invention is to solve the above problems. The present inventor has found that a crystalline antimicrobial composition obtained from silica gel, which is a main component of the amorphous antimicrobial composition, is capable of improving a physical property of an antimicrobial polymer composition and improving heat resistance as well as weatherability through a conversion of parent body of silica gel, which is the frame-work of amorphous antimicrobial composition, into a crystal form.

Furthermore, an antimicrobial ceramic composition comprising the crystalline antimicrobial composition of the present invention exhibits excellent biocidal activity and weatherability, as well as heat resistance and discoloration resistance thereof are far superior to those of a composition comprising a conventional inorganic antimicrobial compound.

SUMMARY OF THE INVENTION

The present invention provides a crystalline antimicrobial composition comprising crystalline silicon dioxide containing silver ions and one or two optional metal ions selected from the group consisting of zinc and copper. The present invention also provides a process for preparing said crystalline antimicrobial composition comprising the steps of: 1) preheating an antimicrobial composition having an antimicrobial coat of an aluminosilicate provided on the surface of silica gel, wherein said aluminosilicate contains silver ions and one or two optional metal ions selected from the group consisting of zinc and copper, to a temperature of between 250° and 500° C. to thereby substantially remove water and : 2) sintering the antimicrobial composition at a temperature of from 800° to 1300° C.

The present invention further provides an antimicrobial ceramic composition comprising a ceramic and said crystalline antimicrobial composition.

DETAILED EXPLANATION OF THE INVENTION

Figure 1:
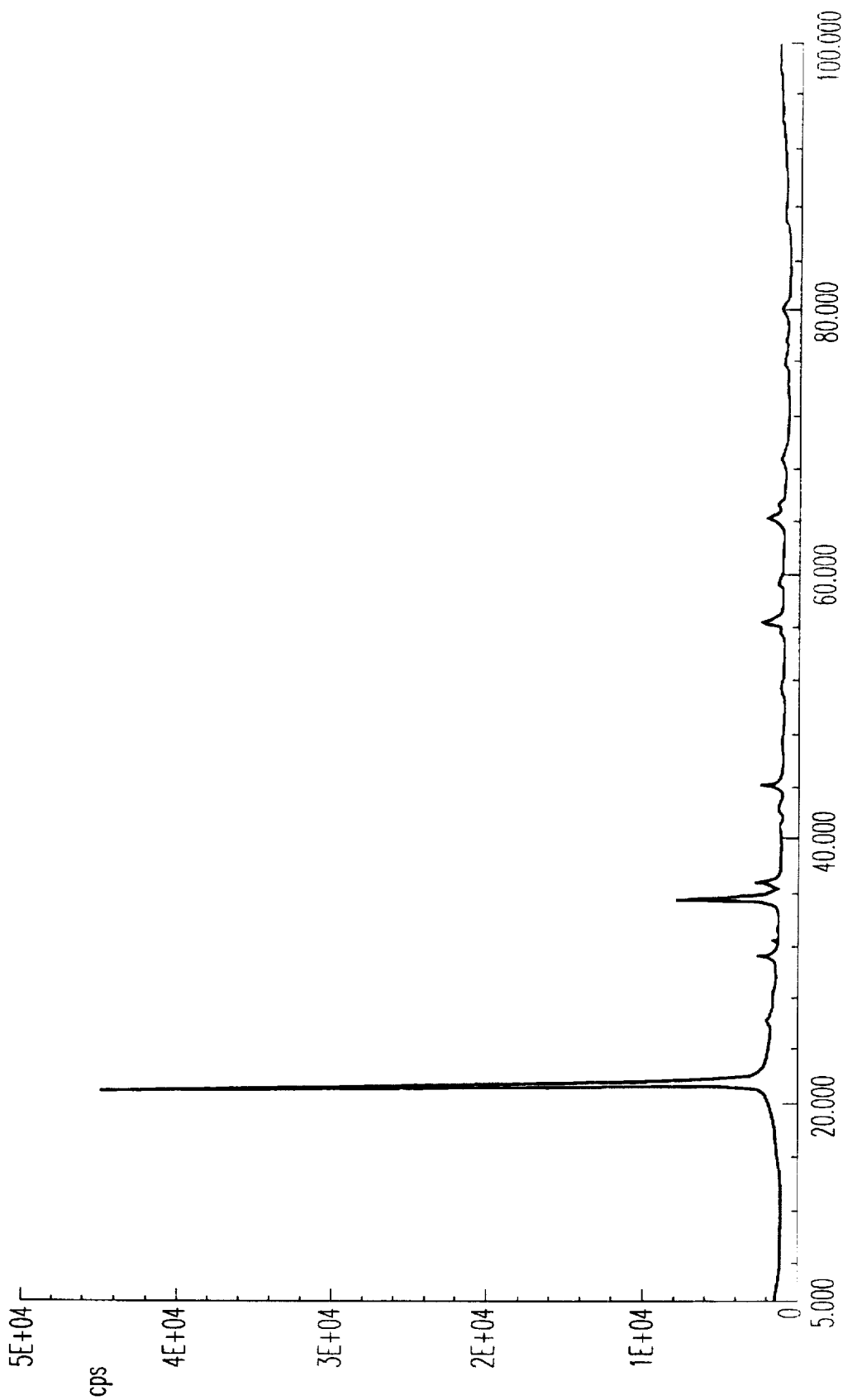
FIG. 1 shows an X-ray diffraction spectrum of the antimicrobial composition of sample 7 (Ag=3.7%, Zn=2.0%: Dav=3.77 microns). The ordinates axis represents relative intensity and the transverse axis represents a diffraction angle.

The present invention provides a crystalline antimicrobial composition comprising crystalline silicon dioxide containing silver ions and one or two optional metal ions selected from the group consisting of zinc and copper.

In the present invention, a crystal form of the crystalline antimicrobial composition is not restricted. However, a cubic or cristobalite system is preferred, furthermore a crystalline ratio is not restricted either. However, crystalline antimicrobial composition of the present invention is desirable to have a crystalline ratio of preferably at least 50%, more preferably 70–100%. The crystalline silicon dioxide which is a parent body of the antimicrobial composition of the present invention is mainly composed of crystalline silicon dioxide as is clearly revealed by the later mentioned X-ray diffraction analysis. Said main component of silicon dioxide comprises preferably at least 70 wt %, more preferably at least 75 wt %, most preferably at least 79 wt % of the antimicrobial composition of the present invention. Additionally, the composition of the present invention may contain preferably 15 wt % or less of aluminum oxide ($Al_2O_3$), more preferably 11 wt % or less and, most preferably 8 wt % or less. Further, zinc and copper also can be employed as a biocidal metal together with silver.

Silver must be contained as an essential biocidal metal in the antimicrobial composition of the present invention. Silver ions comprise preferably at least 0.3 wt %, more preferably at least 0.5 wt %, most preferably at least 1 wt % of the antimicrobial composition of the present invention. Furthermore, the crystalline antimicrobial composition of the present invention can contain silver ions solely or silver ions and at least one type of biocidal metal ion selected from the group consisting of zinc ions and copper ions as biocidal metal ions.

In case of that zinc ions and copper ions are present in the antimicrobial composition of the present invention, a preferable amount thereof is 1–5 wt % and 0.3–4 wt %, respectively. The crystalline antimicrobial composition of the present invention is able to comprise also non-biocidal metal ions having a valence of 1 to 3. The crystalline antimicrobial composition of the present invention has a bulk density preferably in the range of from 0.4 to 1.4, more preferably from 0.45 to 1.3.

The crystalline antimicrobial composition of the present invention is porous and has a large specific surface area (SSA). As for a pore volume, it has a pore volume of at least 0.3 cm³/g, and one having a pore volume(PV) of from 0.4 to 1.0 cm³/g is preferred. The crystalline antimicrobial composition of the present invention has a SSA of at least 5 cm²/g, and one having a SSA of from 25 to 450 cm²/g is more preferred. A SSA is measured by the $N_2$ gas adsorption method of BET method and PV is measured by the aid of the mercury porosimeter.

The process for producing the antimicrobial composition of the present invention is described below.

An antimicrobial composition having an antimicrobial coat of an aluminosilicate on the surface of a silica gel, wherein said aluminosilicate containing silver ions and one or two optional metal ions selected from the group consisting of zinc and copper is used as a starting material. Furthermore, said starting material can contain non-biocidal metal ions with valences either 1, 2 or 3 or ammonium ions.

The process for preparing said starting material is well known as disclosed in Japanese Patent Publication (kokoku) No. 39368/94 and U.S. Pat. No. 5,244,667 and briefly stated below.

The process comprises a first step of chemically treating a porous silica gel with an alkali solution and an aluminate solution and then forming an antimicrobial coat on the thus-treated surface of the silica gel and the second step of treating with a salt solution comprising at least one type of antimicrobial metal ion to allow antimicrobial metal ions [$Ag^+$ and optional $Zn^{2+}$ and/or $Cu^{2+}$] to be retained in the aluminosilicate coat. In the first step, aluminic acid ions [$Al(OH)_4^-$; $AlO_2 \cdot 2H_2O$] react with $Si(OH)_4$ [$SiO_2 \cdot 2H_2O$ as a monomer] present on a surface of pores (micro pore and/or macro pore) in the silica gel to form negatively charged aluminosilicate ions. A firm ionic bond is formed with between aluminosilicate layer and porous silica gel so that the release of the aluminosilicate layer from the porous silica gel is completely prevented.

In the second step, an ion-exchange treatment is carried out in order to retain antimicrobial and/or microbial ion of $Ag^+$ and optional $Zn^{2+}$ and $Cu^{2+}$ ions in the thin aluminosilicate layer. By the above process, antimicrobial metal ions are exchanged with ion exchangeable metal ion in the aluminosilicate layer and thus the formed antimicrobial layer is strongly fixed on the surface of silica gel pores. Through the above procedure, the staring material of the crystalline antimicrobial composition of the present invention is prepared.

Next, the process for preparing the crystalline antimicrobial composition of the present invention is described below.

A predetermined amount of necessary antimicrobial metal ions in the starting material is able to present in the form of single or composite metal ion, i.e. $Ag^+$—$Zn^{2+}$, $Ag^+$—$Cu^{2+}$, and $Ag^+$—$Zn^{2+}$—$Cu^{2+}$. The starting material can contain non-biocidal metal ion with valences of 1 to 3, such as alkali metal ions, divalent nickel and other alkaline earth metal ions, and trivalent rare earth elements [lanthanoid elements: $Ln^{3+}$, elements having an atomic number of from 58 to 71, 21 (Sc), 39(Y) and 57(La)] and zirconium (in a form of zirconyl:$ZrO^{2+}$). Furthermore, said starting material can contain ammonium ions, such as $NH_4^+$, $C_7H_{15}N_2^+$, $C_3H_{16}N^+$, $Me_4N^+$(TMA:tetramethylammonium ion), $Et_4N^+$ (TEA:tetraethylammonium ion), and $Pr_4N^+$ ((TPA:tetrapropylammonium ion).

The presence of said non-biocidal ions in the starting material contributes to improve physical properties as well as antimicrobial effects of the obtained antimicrobial composition.

An amorphous antimicrobial composition comprising a silica gel body is prepared by the above-mentioned process and comprises a silica as a major component thereof. It comprises preferably at least 70 wt % of $SiO_2$ and 15 wt % or less of alumina ($Al_2O_3$). It further comprises antimicrobial metal ions, such as Ag, Zn and Cu, and an optional non-biocidal metal ions having a valence of 1 to 3. Such an antimicrobial composition has a large SSA and lead to porous. Furthermore, all of components have good heat resistance. Accordingly, such an antimicrobial composition is preferable as a starting material of the antimicrobial composition of the present invention. A form of the starting material is not restricted in the present invention and it is possible to be employed in a form of a fine powder, a ground particle or a formed body.

The SSA of the porous starting material is large enough to be in the range of 350–600 $M^2/g$. Since all of said components are structured of inorganic substances, the starting material has excellent heat resistance. Accordingly, in the thermal treatment of the starting material followed by crystallization, there is no loss of each inorganic component and the chemical composition remains unchanged. By the use of such a starting material, the SSA and PV decrease is kept to a preferable degree and the thus-obtained particles can be fined easily. Such a process leads to an increase in a biocidal rate of the obtained antimicrobial composition.

It is stated that the staring material can contain ammonium ions. This is sometimes preferable due to the following advantageous effects. The silica gel containing $NH_4^+$ is used as a starting material in the after mentioned working example 11. When a crystallization step is performed by sintering at high temperature, a decomposition gas is generated and numerous micro voids are produced in the body. The formation of micro voids makes the obtained antimicrobial composition more porous and inhibits a decrease in SSA so that the produced antimicrobial composition has a preferable bulk density and SSA level. Such an antimicrobial composition is possible to contact with fungi effectively and its biocidal rate is increased, significantly.

As mentioned above, the starting material containing non-biocidal metal ions can be used. In the after-mentioned working examples, the amorphous antimicrobial composition containing zirconyl ions ($ZrO^{2+}$), rare earth element ions (lanthanum ion; $La^{3+}$) and divalent metal ions (calcium ion; $Ca^{2+}$) are used as starting materials of the samples 9, 10 and 12, respectively. When these materials are sintered and converted to a crystalline antimicrobial composition, the presence of $Zr^{2+}$, $La^{3+}$ or $Ca^{2+}$ ion improves heat resistance, weatherability and resistance to discoloration. Furthermore, biocidal ability is increased because of the difference in bonding energies between antimicrobial metal ions ($Ag^+$, $Zn^{2+}$ and $Cu^{2+}$) and non-biocidal metal ions ($La^{3+}$ and $ZrO^{2+}$).

The crystalline antimicrobial composition can be prepared from said amorphous antimicrobial composition by carrying out the following two step heat treatment.

The first step of the treatment involves keeping the temperature from 250° to 500° C. under atmospheric pressure or vacuum pressure to substantially remove water contained in an antimicrobial composition. The second step is to sinter the composition at high temperature to convert the amorphous antimicrobial composition to a crystalline antimicrobial composition. In this case, a sintering temperature and sintering time vary depending on the composition of the starting material. Generally,the said treatment is carried out at a temperature range of from 800° to 1300° C. for 1 to 3 hours. By means of the above treatment, an crystalline antimicrobial composition comprising crystalline Silicon dioxide as a major component is prepared.

The expression "to substantially remove almost amount of water contained in an antimicrobial composition" means to remove water adsorbed on the surface of the composition. The temperature during the second treatment step is in the range of from 800° to 1300° C., preferably. When the temperature is below 800° C., crystallization is not fully accomplished and an antimicrobial polymer composition comprising the obtained antimicrobial composition has less weatherability. When the temperature is higher than 1300° C., crystallization is fully accomplished. However, if the sintering is carried out at a temperature higher than 1300° C., the antimicrobial ability of the composition tends to decrease with an increase of the temperature. Accordingly, it is preferable to conduct sinter at the temperature below 1300° C. in order to inhibit a decrease of antimicrobial ability of the obtained composition. The more preferable temperature range for the second step treatment is from 850° to 1200° C.

The sintered product has a trend to coagulate and is glassy or in ceramic form. It is ground or granulated to a predetermined particle size. A bulk density of the ground crystalline antimicrobial composition varies depending on the physical properties and composition of the starting material or temperature of the heat-treatment. Preferably, the bulk density is in the range of from 0.4 to 1.4. Because such a crystalline antimicrobial composition has excellent biocidal ability. Furthermore, such a crystalline antimicrobial composition is preferable for combining with a ceramic to provide a uniform mixture having a good dispersibility.

Therefore, the present invention further provides an antimicrobial ceramic composition comprising a crystalline antimicrobial composition of the present invention and a ceramic.

The antimicrobial ceramic composition of the present invention is preferably used for sanitary ware or tiling. Commercial inorganic tiling or sanitary ware typically comprises $SiO_2$(61 wt %), $Al_2O_3$(7.8 wt %) and CaO(11.5 wt %) as major components and $Fe_2O_3$, $K_2O$, $Na_2O$, $Fe_2O_3$, MgO, $P_2O_5$, $ZrO_2$ and ZnO as minor components. The above materials are wet molded, dried and finally sintered at a temperature higher than 1000 ° C. in order to prepare the sanitary ware or tiling. When used in the above field, it is desirable for biocidal compounds to have a good heat resistance, a stable structure at a temperature higher than 1000° C. and good discoloration resistance. Furthermore, it is desirable for the biocides to maintain their biocidal activity after a sintering at a high temperature, such as 1000°–1200° C.

Furthermore, a reduced cohesiveness of biocidal particles providing an easy application of a uniform biocidal coating on a surface of a tiling and a sanitary ware are desired. A crystalline antimicrobial composition of the present invention satisfies all of the above requirements as such it is preferably used for preparing biocidal tiling and sanitary ware.

A crystalline antimicrobial composition of the present invention reveals excellent biocidal ability after treatment at high temperatures such as 1200° C. and shows no variance over time.

A particle size of the crystalline antimicrobial composition of the present invention is not restricted and can be changed due to an end use and particle size of ceramics used together.

Particles having sizes of 548-149 microns (30–100 mesh) are generally used, however those having sizes of 300 mesh or much finer particles with sizes of from several microns can be also used. As shown in the later-mentioned working example, an antimicrobial ceramic composition comprising at least 0.2 wt % of the crystalline antimicrobial composition of the present invention exhibits excellent biocidal ability, good stability and preferable resistance to discoloration.

The crystalline antimicrobial composition of the present invention has the following advantages:

(1) Although a structure of the starting material of silica-based amorphous antimicrobial composition is destroyed by high temperature sintering, both SSA and bulk density are kept within the desired range. Accordingly, the obtained particles exhibit an excellent antimicrobial effect against fungi. They also contribute to good mildewcidal effects. For example, a biocidal rate of the antimicrobial composition of the present invention is somewhat slower than that of the starting material, i.e. a silica-based amorphous antimicrobial composition, it shows still excellent antimicrobial effects. The important advantageous effects of the crystalline antimicrobial composition of the present invention are that it has excellent heat resistance, weatherability, light-resistance and discoloration resistance. The crystalline antimicrobial composition of the present invention is still stable at the temperature range of 1200°–1300° C.

Thus, the discoloration of the composition is not observed. A structure of the present crystalline antimicrobial composition is stable against light and a light-resistance is extremely large. Accordingly, when the crystalline antimicrobial composition of the present invention is mixed with a ceramic, a composition having excellent antimicrobial effects, weatherability, light-resistance and discoloration resistance is obtained.

The present invention is described in detail by working examples. However they are not intended to restrict the scope of the present invention.

EXAMPLE 1

This example shows a process for preparing the crystalline antimicrobial composition of the present invention.

The starting materials of antimicrobial composition, as shown in the working examples 1–7 are silica gel based antimicrobial composition composed of 70 wt % or more of $SiO_2$, 15 wt % or less of $Al_2O_3$ and Ag and Zn as antimicrobial metals. It further comprises a small amount of monovalent alkali metal ($Na^+$) as a non-antimicrobial metal ion. The above powdery starting material is preheated at 350° C. for 1 hour as shown in Table 1 in order to substantially remove water is removed. After that, a high temperature sintering step is carried out at 800°–1200° C. for 1 or 2 hours as shown in the Table so as to obtain the present crystalline antimicrobial composition. The obtained clump of sintered body is ground and then finely milled with a JET mill. The samples 1–7 which comprise the crystalline antimicrobial composition of the invention contain 83.38% of $SiO_2$ and 7.56% of $Al_2O_3$, and 3.6–3.7% of Ag and 2.0% of Zn. An average particle size (Dav) of the fine antimicrobial composition particles is in the range of 2.9–8.3 micrometers, and their bulk densities are in the range of 0.40–1.00($d_1$) and 0.46–1.10($d_2$), as represented in Table 1, wherein $d_1$ and $d_2$ represent a lightly packed bulk density and bulk density packed under vibration, respectively. The method for determining them is as follows:

In order to attain a lightly packed bulk density, a powder is placed in a 200 milliliter graduated cylinder, lightly vibrated, and the volume and weight of the powder are then measured after settling.

In the other hand, to attain a bulk density packed under vibration, a powder is put into a 200 milliliter graduated cylinder under vibration, and further vibrated after the powder has been settled, followed by the measurement of the final volume and weight of the powder.

Sample 8 was prepared by the same procedure as that for preparing sample 7 except that the starting material is an antimicrobial composition having a silica gel body containing 7.2% of Ag as an antimicrobial metal as well as a trace amount of $Na^+$ as a monovalent metal ion. The Dav of the pulverized final product is 5.1 micro meters and the $d_1$ and $d_2$ are 0.94 and 1.05, respectively.

Under the conditions shown in the table, sample 9 was prepared by carrying out heat treatment to recrystallize the starting material of an antimicrobial composition having a silica gel body and containing 3.0% of Ag as an antimicrobial metal, 1.9% of Zr in the form of $ZrO^{2+}$(zirconil ion) as a non-biocidal ion and a trace amount of $Na^+$. The Dav of the pulverized final product of sample 9 is 4.2 micro meters and the $d_1$ and $d_2$ values are 0.71 and 0.86, respectively.

Under the conditions shown in the table, sample 10 was also prepared by carrying out heat treatment to recrystallize the starting material of an antimicrobial composition ($SiO_2$=80.89% and $Al_2O_3$=7.56%) having a silica gel body and containing 3.0% of Ag as an antimicrobial metal, 4.8% of $La^{3+}$, which is a typical lanthanoid element, as a non-biocidal ion and a trace amount of $Na^+$. The Dav of the pulverized final product of sample 10 is 6.8 micro meters and the $d_1$ and $d_2$ values are 0.98 and 1.21, respectively.

Sample 11 was prepared by carrying out a two step heat treatment of the first step at 350° C. for 1 hour and the second step at 1100° C. for 2 hours employing the starting material of an antimicrobial composition ($SiO_2$=79.68% and $Al_2O_3$=7.56%) having a silica gel body and containing 4.0% of Ag and 2.9% of Zn as antimicrobial metals, 3.5% of $NH_4^+$, which is a typical ammonium ion, as a non-biocidal ion and a trace amount of $Na^+$. The Dav of the pulverized final product of sample 11 has a value of 4.5 micro meters and the $d_1$ and $d_2$ are 1.01 and 1.19, respectively.

Under the heat treatment shown in the table, sample 12 was prepared from a starting material of an antimicrobial composition comprising $SiO_2$=81.85% and $Al_2O_3$=7.56% as a silica gel body and containing 2.98% of Ag, 2.01% of Zn, 0.47% of Cu as antimicrobial metal ions, 2.11% of $Ca^{2+}$ as a divalent non-biocidal ion and a trace amount of $Na^+$. The Dav of the pulverized final product of sample 12 is 8.0 micro meters and the $d_1$ and $d_2$ are 1.06 and 1.25, respectively.

The comparative sample 1 is an amorphous antimicrobial composition having a silica gel body containing 3.6% of Ag and 2.0% of Zn. This is the starting material of the samples 1–6. The comparative sample 2 is an amorphous antimicrobial composition having a silica gel body and containing 3.6% of Ag and 2.2% of Zn. The bulk densities of the present antimicrobial composition are very large compared with those of comparative examples 1 and 2.

FIG. 1 shows an X-ray diffraction spectrum of the antimicrobial composition of the present invention (Ag=3.7% and Zn=2.0%; Dav=3.77 micro meters). The analysis reveals that a major crystalline structure of the present composition is $SiO_2$.

It is recognized from the X-ray diffraction spectrum that crystalline of $Zn_2SiO_4$, $ZnSiO_3$, $Al_{16}Si_2O_{13}$, $Al_2SiO_5$, $Al_2Si_4O_{10}$, $Ag_2SiO_3$, $Zn_2SiO_4$, $Ag_4SiO_4$ and $Ag_4Al_{22}O_{37}$ are also contained in the antimicrobial composition of the present invention.

Furthermore, the existence of Ag and Zn as biocidal metals is also confirmed.

TABLE 1

| | Heat treatment | | Content of primary metals contained in the obtained antimicrobial composition | Bulk density of antimicrobial composition | | Average particle size of pulverized antimicrobial composition |
|---|---|---|---|---|---|---|
| Sample No. | First step | Second step | % (anhydrous basis) | $d_1$ | $d_2$ | Dav, μm |
| 1 | 350° C. - 1 hr | 800° C. - 1 hr | Ag = 3.6; Zn = 2.0 | 0.41 | 0.53 | 2.9 |
| 2 | 350° C. - 1 hr | 300° C. - 2 hr | Ag = 3.6; Zn = 2.0 | 0.40 | 0.46 | 3.1 |
| 3 | 350° C. - 1 hr | 900° C. - 1 hr | Ag = 3.6; Zn = 2.0 | 0.56 | 0.65 | 3.7 |
| 4 | 350° C. - 1 hr | 900° C. - 2 hr | Ag = 3.6; Zn = 2.0 | 0.68 | 0.83 | 3.9 |
| 5 | 350° C. - 1 hr | 1000° C. - 1 hr | Ag = 3.6; Zn = 2.0 | 0.83 | 1.10 | 5.3 |
| 6 | 350° C. - 1 hr | 1200° C. - 2 hr | Ag = 3.6; Zn = 2.0 | 0.82 | 1.14 | 8.3 |
| 7 | 350° C. - 1 hr | 1000° C. - 2 hr | Ag = 3.7; Zn = 2.0 | 1.00 | 1.10 | 3.77 |
| 8 | 350° C. - 1 hr | 1000° C. - 2 hr | Ag = 7.2 | 0.94 | 1.05 | 5.1 |
| 9 | 350° C. - 1 hr | 900° C. - 2 hr | Ag = 3.0; Zn = 1.9 | 0.71 | 0.86 | 4.2 |
| 10 | 350° C. - 1 hr | 1100° C. - 1 hr | Ag = 3.0; La = 4.8 | 0.98 | 1.21 | 6.8 |
| 11 | 350° C. - 1 hr | 1100° C. - 2 hr | Ag = 4.0; Zn = 2.9 | 1.01 | 1.19 | 4.5 |
| 12 | 350° C. - 1 hr | 1100° C. - 1 hr | Ag = 2.98; Zn = 2.01; Cu = 0.47; Ca = 2.11 | 1.06 | 1.25 | 8.0 |
| C-1 | dried sample | — | Ag = 3.6; Zn = 2.0 | 0.30 | 0.33 | 2.7 |
| C-2 | dried sample | — | Ag = 3.6; Zn = 2.2 | 0.31 | 0.33 | 2.6 |

C: Comparative Examples
$d_1$: lightly packed bulk density
$d_2$: bulk density packed under vibration

EXAMPLE 2

The antimicrobial power of the crystalline antimicrobial composition of the present invention is discussed below.

To prepare a cell suspension of bacterium, the cells of a test bacterium (*Escherichia coli*) that had been cultivated in an agar medium at 37° C. for 18 hours were suspended in a phosphate buffer ($\frac{1}{15}$M, pH=7.2) at a concentration of $10^6$ cells/ml and diluted appropriately for the test.

To prepare a cell suspension of fungus, the conidia of the test fungus that had been cultivated in a potato dextrose agar medium at 25° C. for 7 days were suspended in 0.005% dioctyl sodium sulfosuccinate aqueous solution to prepare a suspension at a concentration of $10^8$ cells/ml and diluted appropriately for the test.

Test bacteria: *Escherichia coli* IFO-12734
*Aspergillus niger* IFO-4407
Medium
  fungi: Sabouraud Dextrose Agar (BBL)
  bacteria: Mueller Hinton 2 (BBL)
Test procedure for measuring antimicrobial power:
An antimicrobial sample in the form of a fine powder was determined by "shake flask method (S.F. method)." A predetermined amount of dried fine powder of antimicrobial composition was added to a phosphate buffer solution in a 200 -ml volumetric flask. When *Escherichia coli* was tested, 15 mg of the sample was used, while when *Aspergillus niger* was tested, 50 mg of the sample was used. The test fungi or bacteria suspension was added to make a total volume of 100 ml and a number of cells were adjusted to those represented in Tables 2 and 3. The flask was shaken at 25° C.±1° C. and a number of viable cells were measured at predetermined periods.

It can be seem from the result shown in Table 2, that the antimicrobial compositions of samples 1–5, 8 and 10 (Dav= 2.9–6.8 micro meters) killed almost all *E. coli* in a short period, i.e. within about 60 minutes. The control examples 1 and 2 were blank tests, carried out without an antimicrobial composition.

Table 3 represents a result of a measurement of antimicrobial power against *A. niger*. The antimicrobial power was measured by a shake flask method with $10^5$ cells/ml of an initial count of *A. niger* cells and 50 mg/100 ml of a concentration of the antimicrobial composition. As shown in the table, a preferable result was obtained. The sample 2 was sintered at 800° C. for 2 hours and sample 3 was sintered at 900° C. for 1 hour. Both samples 2 and 3 exhibit good antimicrobial activity and almost all of *A. niger* was killed within 8 hours. The sample 3, which was sintered at a temperature above 1000° C., has less antimicrobial power against *A. niger* than that of the samples 2 or 3. The comparative example 1 shown in the table 3 is the same sample as in table 1.

It is obvious from the results shown in the tables 2 and 3, that the present crystalline antimicrobial composition comprising crystalline silicon dioxide as a principle component shows satisfactory antimicrobial power against common fungus and bacterium.

Samples 4, 6 and 10, which are within the scope of the present invention, were press molded. Furthermore, a known antimicrobial zeolite having a zeolite body containing $SiO_2$ and $Al_2O_3$ at a molar ratio of $SiO_2/Al_2O_3=1.99$ and comprising 3.4% of Ag and 6.9% of Zn was also press molded. The press molded test pieces have a diameter of 30 mm and a thickness of 5 mm. These samples were exposed to UV radiation (365 nm) for 500 hours under the same conditions. No discoloration was observed and no change occurred with time with respect to the 3 samples of the present invention. On the other hand, with respect to the comparative sample of the known antimicrobial zeolite discoloration was observed after 140–150 hours. It is revealed from the above test that a crystalline antimicrobial composition of the present invention has excellent weatherability.

TABLE 2

Measuring method: shake flask method (S.F. method)
Bateria: *Escherichia coli*(IFO 12734)
Initial cell count: $10^5$/ml
Total liquid volume: 100 ml

| | | Antimicrobial composition | | Number of viable cells per ml | | | |
|---|---|---|---|---|---|---|---|
| | | Amount | Antimicrobial metal content | | | | |
| Sample No. | Dav, μm | mg/100 ml | mg/100 ml | 0 min. | 20 min. | 60 min. | 180 min. |
| 1 | 2.9 | 15 | Ag = 0.54; Zn = 0.30 | $2.1 \times 10^5$ | 0 | 0 | — |
| control - 1 | — | — | — | $2.1 \times 10^5$ | $1.8 \times 10^5$ | $1.7 \times 10^5$ | — |
| 2 | 3.1 | 15 | Ag = 0.54; Zn = 0.30 | $3.2 \times 10^5$ | 0 | 0 | 0 |
| 3 | 3.7 | 15 | Ag = 0.54; Zn = 0.30 | $3.2 \times 10^5$ | 0 | 0 | 0 |
| 4 | 3.9 | 15 | Ag = 0.54; Zn = 0.30 | $3.2 \times 10^5$ | — | — | 2 |
| 5 | 5.3 | 15 | Ag = 0.54; Zn = 0.30 | $3.2 \times 10^5$ | $9.1 \times 10^4$ | 5 | 3 |
| 8 | 5.1 | 15 | Ag = 1.1 | $3.2 \times 10^5$ | 0 | 0 | 0 |
| 10 | 6.8 | 15 | Ag = 0.45 | $3.2 \times 10^5$ | $1.1 \times 10^1$ | 6 | 0 |
| control - 2 | — | — | — | $3.2 \times 10^5$ | $3.4 \times 10^5$ | $2.4 \times 10^5$ | $2.2 \times 10^5$ |

TABLE 3

Measuring method: shake flask method (S.F. method)
Fungi: *A. niger* (IFO 4407)
Initial cell count: $10^5$/ml

| | | Antimicrobial composition | | Number of viable cells per ml | | |
|---|---|---|---|---|---|---|
| | | Amount | Antimicrobial metal content | | | |
| Sample No. | Dav, μm | mg/100 ml | mg/100 ml | 0 hr | 3 hr | 8 hr |
| 2 | 3.1 | 50 | Ag = 1.8; Zn = 1.0 | $1.4 \times 10^5$ | $1.3 \times 10^2$ | 0 |
| 3 | 3.7 | 50 | Ag = 1.8; Zn = 1.0 | $1.4 \times 10^5$ | $1.8 \times 10^3$ | 9 |
| 5 | 5.3 | 50 | Ag = 1.8; Zn = 1.0 | $1.4 \times 10^5$ | $7.7 \times 10^4$ | $2.3 \times 10^4$ |
| C - 1 | 2.7 | 50 | Ag = 1.8; Zn = 1.0 | $1.4 \times 10^5$ | 5 | 0 |
| control | — | — | — | $1.4 \times 10^5$ | — | $2.7 \times 10^5$ |

C - 1: Comparative Examples 1

EXAMPLE 3

This example shows a process for preparing antimicrobial tiling comprising the antimicrobial composition of the present invention and evaluation of the produced tile.

The crystalline antimicrobial composition of sample 7 was added to a commercial acrylic emulsion paint and mixed to a uniform dispersion. Said acrylic emulsion paint comprises 70% of acrylic emulsion, 10% of $TiO_2$, 10% of hydroxyethyl cellulose, 8% of Demol EP 25% solution and 2% of water. The content of the sample 7 was 10%.

The obtained mixture was coated three times on the surface of a ceramic tile to form a uniform coating layer. Sample piece T-A was prepared by air drying. Sample piece T-B was prepared by preheating the sample piece T-A at 450–500° C. and sintering it at about 1000° C. for 2 hours.

An antimicrobial activity test of the obtained sample pieces T-A and T-B was carried out by a drop method using *E. coli*. An initial cell count was kept at $10^5$ cells per piece and a number of viable cells was counted after 24 hours and 48 hours. As shown in table 4, the antimicrobial tile of the present invention exhibits excellent antimicrobial activity. Furthermore, it is confirmed that a sintered sample piece T-B shows excellent weatherability and no discoloration occurs over time.

TABLE 4

| Test sample | A number of E. coli* (hr) | | |
|---|---|---|---|
| | 0 | 24 | 48 |
| T - A | $2.7 \times 10^5$ | <10 | — |
| T - B | $2.7 \times 10^5$ | — | $2.2 \times 10^1$ |

*a number per a piece of tile

I claim:

1. A crystalline antimicrobial composition comprising crystalline silicon dioxide as a major component, said crystalline silicon dioxide contains silver ions and one or two optional metal ions selected from the group consisting of zinc and copper.

2. A crystalline antimicrobial composition of claim 1 wherein a content of crystalline silicon dioxide is at least 70 wt %.

3. A crystalline antimicrobial composition of claim 1 wherein a bulk specific gravity is from 0.4 to 1.4.

4. A crystalline antimicrobial composition of claim 1 wherein a content of silver ions is at least 0.3 wt %.

5. A process for preparing a crystalline antimicrobial composition of claim 1 comprising steps of 1) preheating an antimicrobial composition having an antimicrobial coating of an aluminosilicate provided on the surface of silica gel, wherein said aluminosilicate contains silver ions and one or two optional metal ions selected from the group consisting of zinc and copper, to a temperature between 250° and 500° C. to substantially remove water and 2) sintering at a temperature from 800° to 1300° C.

6. An antimicrobial ceramic composition comprising a ceramic and crystalline antimicrobial composition of claim 1.

7. An antimicrobial ceramic composition of claim 6 wherein the composition is formed into sanitary ware or tiling.

8. An antimicrobial ceramic composition of claim 6 wherein a content of the crystalline antimicrobial composition is at least 0.2 wt %.

9. An antimicrobial ceramic composition comprising a ceramic and crystalline antimicrobial composition of claim 2.

10. An antimicrobial ceramic composition comprising a ceramic and crystalline antimicrobial composition of claim 3.

11. An antimicrobial ceramic composition comprising a ceramic and crystalline antimicrobial composition of claim 4.

12. An antimicrobial ceramic composition of claim 9 wherein the composition is formed into sanitary ware or tiling.

13. An antimicrobial ceramic composition of claim 10 wherein the composition is formed into sanitary ware or tiling.

14. An antimicrobial ceramic composition of claim 11 wherein the composition is formed into sanitary ware or tiling.

15. An antimicrobial ceramic composition of claim 9 wherein a content of the crystalline microbial composition is at least 0.2 wt %.

16. An antimicrobial ceramic composition of claim 10 wherein a content of the crystalline microbial composition is at least 0.2 wt %.

17. An antimicrobial ceramic composition of claim 11 wherein a content of the crystalline microbial composition is at least 0.2 wt %.

* * * * *